United States Patent [19]
Bacus

[11] Patent Number: 5,078,969
[45] Date of Patent: Jan. 7, 1992

[54] MAGNETIC STIRRER

[75] Inventor: James W. Bacus, Hinsdale, Ill.

[73] Assignee: Cell Analysis Systems, Inc., Elmhurst, Ill.

[21] Appl. No.: 450,815

[22] Filed: Dec. 14, 1989

[51] Int. Cl.$^5$ .............................................. B01L 3/00
[52] U.S. Cl. .................................. 422/99; 422/300; 118/423; 118/500; 366/274; 134/201
[58] Field of Search ............... 422/99, 300; 118/423, 118/500; 156/57; 356/36; 366/273, 274; 134/201

[56]     References Cited
       U.S. PATENT DOCUMENTS

| | | | |
|---|---|---|---|
| 2,350,534 | 6/1944 | Rosinger | 259/108 |
| 3,378,878 | 4/1968 | Shoemaker | 134/188 |
| 3,421,528 | 1/1969 | Gomez et al. | 134/188 |
| 4,131,370 | 12/1978 | Lawrence et al. | 366/273 |
| 4,162,855 | 7/1979 | Bendar | 366/274 |

Primary Examiner—Robert J. Warden
Assistant Examiner—Laura E. Collins
Attorney, Agent, or Firm—Fitch, Even, Tabin & Flannery

[57]     ABSTRACT

An apparatus and method for staining cell objects on microscope slides includes a container for holding a staining solution and for holding one or more of the slides having the cell objects thereon. The container is preferably a Coplin jar in which is disposed a perforated cage containing a magnetic stirrer. Lower ends of the slides rest on the top of the cage and the stirrer drives liquid in and out of the cage and stirs and mixes the stain solution to obtain uniformity of stain concentration throughout the Coplin jar. A magnetic drive unit is positioned below the container and magnetic flux travels through the imperforated bottom wall of the glass Coplin jar to couple the stirrer rod to rotate within the cage, as the magnetic driver rotates in the unit beneath the jar.

6 Claims, 1 Drawing Sheet

MAGNETIC STIRRER

BACKGROUND OF THE INVENTION

The present invention relates to a method and apparatus for the preparation of stained cells or cell objects on microscope slides for later use in image analysis or the like.

The variation in degree of staining cell objects and the non-uniformity of the staining of the cell objects on a cell slide presents a problem in the quantification of the stained cell objects by a subsequent image analysis technique. The term "cell objects" as used herein includes not only cells and cellular material such as DNA, but also includes artificial materials such as beads or the like which may be stained and used as a calibration material. The uniformity of staining may not be as important for large or gross evaluations of cellular material on a slide but can be critical in analysis of small cell objects, such as DNA within a cell nucleus. The cell objects are incredibly small for example, 100 micrometers$^2$ in size or less. In such analysis, even small shifts in light transmission due to subtle staining variations can cause particular changes in a later diagnosis or prognosis. These subtle staining shifts may be much too subtle for the human eye; or so small that the human eye and a manual analysis of the cell objects is not affected. That is, the staining technique which is suitable and adequate for the human eye may not be adequate where there is a system using automatic analysis, which makes much finer determinations of grey values when, e.g., determining the absolute value of DNA content of a cell nuclei.

U.S. patent application Ser. No. 076,685 filed July 2, 1987 now abandoned and Ser. No. 121,674 filed Nov. 17, 1987 now U.S. Pat. No. 5,016,283 disclose staining kits which use a number of different staining stains and staining techniques and particularly, Feulgen staining technique to use to stain DNA in cell objects with dyes such as for example, with Thionin on cell objects such as rat liver cells. In addition, as disclosed in other patents and applications directed to this image analysis technique, there is often a need to analyze the morphological features such as the texture in combination with the size and shape of the cell nuclei and/or alterations in the nuclear cytoplasmic ratios of cells, all of which are dependent upon an accurate and uniform staining.

There are a number of available staining techniques which can be used. The Feulgen staining technique may be used to stain DNA in cell objects with dyes, for example, with Thionin, Azure A, Azure C, pararosanilin and methylene blue. Proteins may be stained with congo red, eosin, an eosin/hematoxylin combination, or fast green. Enzymes may be made visible with diaminobenzidine or 3-amino-9 ethylcarbazole or alkaline phosphatase in combination with a dye substrate; cell organelles may be stained with methylene blue; and ribosomes with methylene blue and mitochrondia with giemsa stain. Moreover, as used herein, stain includes counter stains such as methyl green. In breast cell cancer analysis some of these stains are used in combination with monoclonal antibodies which detect estrogen receptors. Antigen analysis may include the steps of binding of monoclonal antibodies to the specimen and control cell objects. Later the monoclonal antibody may be conjugated with an enzyme stain. Also, the monoclonal antibody may be conjugated with a fluorescent material. Then the fluorescent stain may be excited at a wavelength to induce the fluorescence and then this may be observed at another wavelength at which fluorescent emission occurs. When the antibody is made for a particular virus, the control cell specimen objects may be treated with a nucleic acid probe specific for the genome of the virus.

As disclosed in another application Ser. No. 121,674 filed Nov. 17, 1987, the staining of the cell population may include staining with an alkaline phosphatase technique using a monoclonal antibody against a specific cytoplasmic antigen. The resulting stain is substantially specific to the cytoplasm and does not stain the nucleus of the cells. A Feulgen staining process using Thionin is then performed to stain the DNA in the nucleus of each cell. The alkaline phosphatase staining method is used because of its compatibility with the Feulgen staining technique. The alkaline phosphatase staining is specific to the cytoplasmic antigen binding the chosen monoclonal antibody and does not harm the nuclear material so that it may receive the Feulgen stain in the subsequent step. The alkaline phosphatase staining is accomplished first before the destruction of the cytoplasm by the Feulgen staining technique. The chromogen chosen for the staining technique is a fast red dye which is advantageous for two reasons. In the first instance, the fast red dye which is precipitated is not susceptible to being washed out by the Feulgen staining process; and thus will remain for the optical visualization. The second reason is that the chromogen provides an excellent optical separation from the blue Thionin dye used in the Feulgen staining process.

Manifestly, there are other dyes and stains other than those listed and described in the aforesaid techniques wherein the staining of cell objects on slides is later used in analysis techniques such as image analysis. The present invention is not to be limited to the particular dyes or stains described above or the particular analysis used or described herein or described in the aforesaid patent applications, each of which is hereby incorporated by reference as if fully reproduced herein. Rather, the present invention is directed to the providing a more uniform staining technique for cell objects on microscope slides wherein staining uniformity is needed such as where there is an absolute value measurement of DNA or measurements of small cell areas or cellular masses in picograms.

In order to obtain the accuracy of measurement desired, the slides may be provided with calibration cell objects and then specimen cell objects to be analyzed are added onto the same slide. Both the calibration cell objects and the specimen cell objects are stained simultaneously; and then the image analysis apparatus is calibrated by comparing the stain on the calibration cell objects to a predetermined known standard, and adjustments are made for the staining deviation from the standard. Such slides having calibration cell objects thereon have been inserted into standard staining containers such as Coplin staining jars having grooves to hold a plurality of vertical slides back-to-back in the jar. Despite care taken in the mixing of the stain in the Coplin jars, it has been found that some stains, such as the Thionin stain, do not provide the same stain intensity. For example, the cells may not be stained the same amount even though they are in the same jar. This results in quality control problems. It has been found that the Thionin dyes are not very soluble in water and that the Thionin dyes sometimes tend to separate into different phases or levels with different stain concentrations in different levels. This may not be not apparent to the naked eye, but this appears, in fact, to be true. It has been found that if one turns several of the slides to have their calibration cells on their upper ends in the Coplin jar, that these calibration cells may have a different stain concentration from the calibration cells on the lower ends of other slides in the same Coplin jar. The slides are usually glass slides and may be easily broken; and the size of the slides and the Coplin jar as well as the amount of stain and the staining techniques have already been developed. Hence, it is desired to continue to use the same slides, stains and Coplin jars but to improve the uniformity of stain concentration in an inexpensive and simple manner.

Accordingly, a general object of the invention is to provide an apparatus and method for improving the uniformity of staining of cell objects on microscope slides.

BRIEF DESCRIPTION OF THE DRAWINGS

In the figures of the drawing, like reference numerals identify like components, and in the drawing.

DETAILED DESCRIPTION OF THE PREFERRED EMBODIMENT

Figure 1:
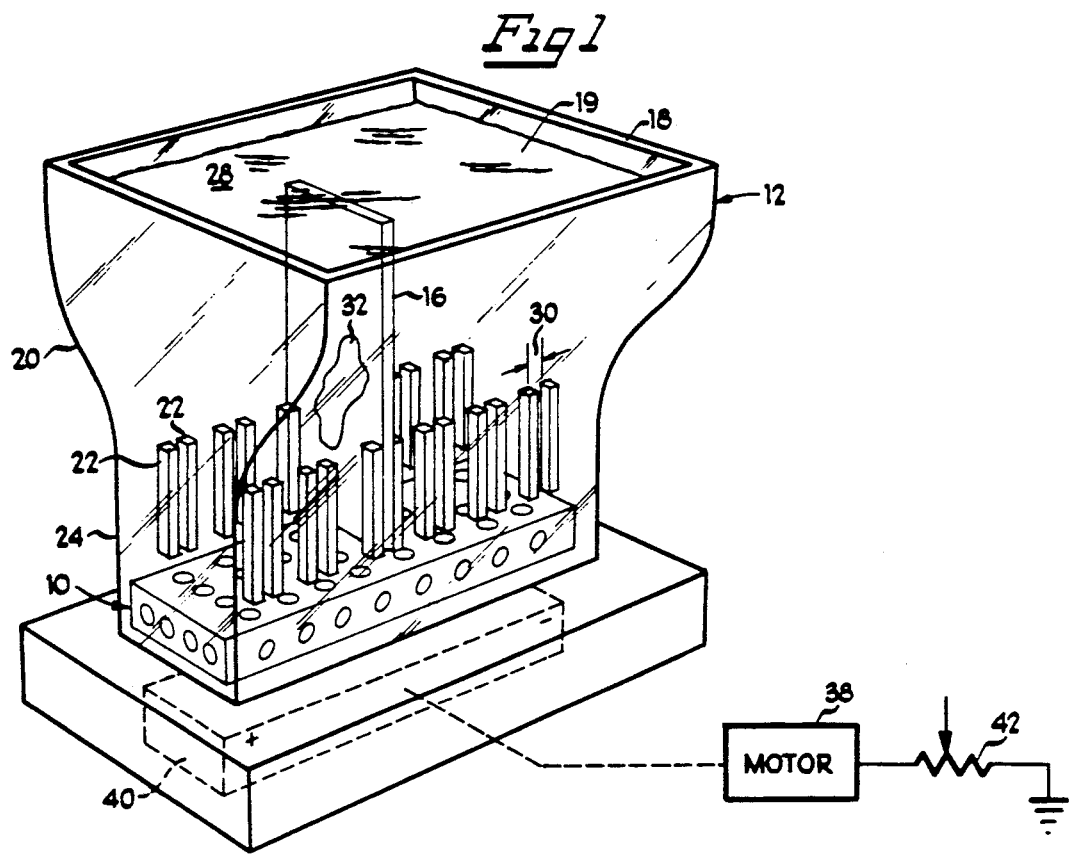
FIG. 1 is a perspective view of a Coplin jar with the stirring rod assembly and a magnetic drive means.

As shown in the drawings for purposes of illustration, there is an apparatus 10 used in the preferred method of providing a more uniform staining of cell objects such as specimen cell objects 15 and calibration cell objects 17 on a microscope slide 16. A stain or staining solution 19 is disposed in a container such as a Coplin jar 12 into which are placed a plurality of slides each having cell objects thereon for staining. Herein, the slides have both the calibration cell objects and the specimen cell objects, but manifestly a single cell object or more than two groups of cell objects can be placed on a slide. A plurality of ribs 22 in the Coplin jar hold a series of slides back-to-back in a vertical array while the staining is occurring.

While not usually visible to the naked eye, it has been found that some stains 19, such as Thionin, are not very soluble in water and tend to separate into two phases, resulting in different stain concentrations at different levels. One of the purposes of staining the calibration cell objects 17 and the specimen cell objects 15 simultaneously with the same staining solution is to eliminate variations in analysis due to staining at two different times or with two different stain solutions. Hence, the different stain concentrations at different levels in the liquid thwarts this calibration technique. Because the slides are glass and because the stain kits and the staining techniques are already formulated for use with a Coplin jar, it is preferred that elimination of non-uniform staining of cell objects either on the same slide or between different slides be attained while using this equipment or comparable equipment.

In accordance with the present invention, more uniform staining of cell objects 15 and/or 17 on a microscopic slide 16 is achieved by a magnetic stirring means which agitates and stirs the stain 19 to maintain a relatively constant solution concentration and to prevent the phase separation that has resulted in non-uniform staining. The preferred magnetic stirring is accomplished by containing a magnetic stirrer preferably in the form of a rod 54, within a cage or housing 50 located at the bottom of the Coplin jar and which supports lower ends 33 of the microscope slides. The cage 50 is perforated at perforations or holes to allow the liquid stain to flow into and through the perforations which provide small turbulent jets of incoming and outgoing liquid stain which mix well and cause a definite flow upwardly and downwardly and throughout the Coplin jar. The cage also contains the stirrer rod 34 within its hollow interior so that the rod is never free to hit the slides or cell objects thereon and is always in position for magnetic coupling to a magnetic drive unit. The preferred cage extends generally co-extensive with the Coplin jar base and is a very small, perforated, plastic, box-shaped piece. The stirrer rod is driven by a magnetic drive 36 which is contained within a very small, flat, box-like unit which will support the Coplin jar. With the jar centered over the magnetic drive 36, a magnetic driver arm 40 in the drive unit is coupled by magnetic force to the stirrer rod to turn the latter as the driver rotates. Thus, there is no perforation in the bottom of the Coplin jar, which is usually made of glass; and the Coplin jar may be easily seated upon or lifted from the top of the drive unit.

Turning now in more specific detail to the illustrated apparatus, it comprises the stirrer subassembly 10 which is placed on the Coplin jar 12 at base 14, as noted in FIG. 1. A Coplin jar is a reaction vessel and frequently used for the staining of biological specimens on microscope slides 16. Jar 12 has a relatively narrow base 14 and a flared or broader mouth 18 with a neck region 20 that is tapered to join base 14 and mouth 18. The base or bottom wall of the jar is imperforated and made of glass so that the magnetic flux passes therethrough to couple the stirrer rod 54 to magnetic drive arm 40. The ribs 22 vertically extend from base 14 along sidewalls 24 and 26 in cavity 28 and are aligned in pairs with slots 30 therebetween to receive a specimen slide 16 with cell objects thereon. Jar 12 is seated on platform 34 with magnetic-stirrer drive 36 mounted and operable below platform 34. Magnetic drive 36 has motor 38 with magnetic drive arm 40 and a variable speed control device 42, which device 42 is coupled between motor 38 and a source of power to control the angular velocity of magnetic arm 40. Magnetic arm 40 is shown as a permanent magnet for illustrative purposes and not as a limitation.

Figure 2:
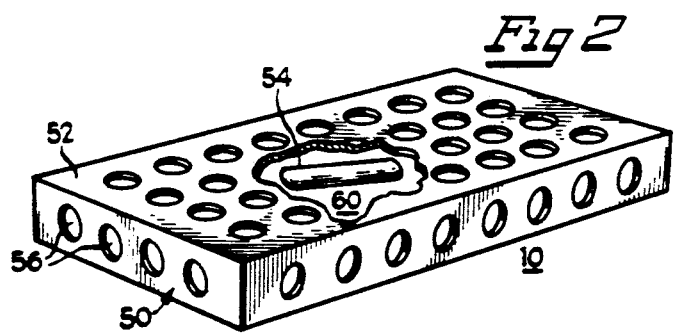
FIG. 2 is an enlarged perspective view of the cage in partial section.

The stirrer subassembly 10 in an enlarged view in FIG. 2 includes the cage or housing 50 with its upper surface 52 broken away to show stirring rod 54 in chamber 60. Housing 50, which is shown with a generally rectangular shape, is nested on base 14 of jar 12 and has a plurality of perforations 56 extending through housing 52 to chamber 60. The arrangement of perforations 56 is shown in an ordered alignment, however, the order or arrangement of the perforations is not a limitation.

Figure 3:
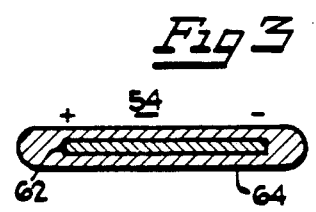
FIG. 3 is an elevational view in cross-section of the stirring rod.
Figure 4:
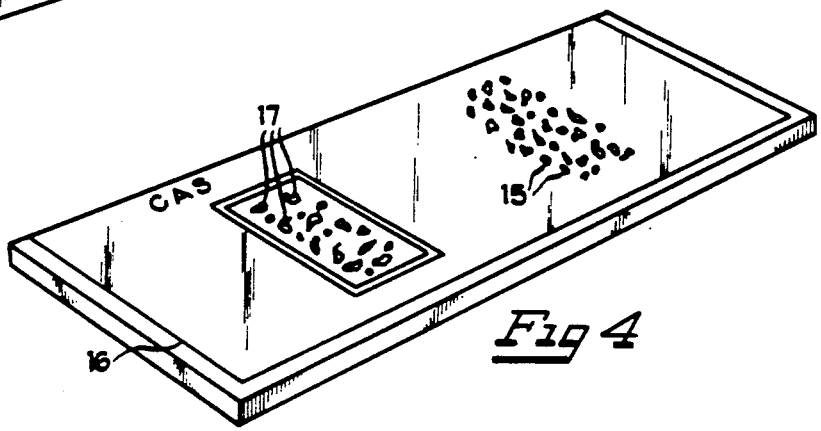
FIG. 4 is a view of a microscopic slide with calibration and specimen cell objects thereon.

Stirring rod 54 in FIGS. 2 and 3 has a magnetic pole piece 62 encased or sheathed in a jacket 64 of a relatively nonreactive material, such as polytetrafluoroethylene (TEFLON), and has the magnetic poles noted thereon as an illustration. Although pole piece 62 may be a permanent magnet it may also be a magnetically responsive material.

Stirrer subassembly 10 is operable with small vessel applications and more particularly is demonstrated with Coplin jar 12 in FIG. 1. Stirring rod 54 in FIG. 1, and more particularly pole piece 62, is alignable with magnetic arm 40 in chamber 60. Motor 38 is energized through variable control 42, which controls the rotational speed of stirring rod 54. As rod 54 is spun in chamber 60 the fluid in jar cavity 28 is agitated by fluid flow through perforations 56. The continuous flow or agitation of the fluid in cavity 28 provides a relatively uniform distribution of any solute in the solution and, therefore, approximately a uniform solution concentration.

In FIG. 1, sample slide 16 with biological specimen cells 15 is positioned in one of slots 30 in cavity 28, and slide 16 rests its lower end on housing upper surface 52. The calibration cell objects 17 are, in this illustrated embodiment, rat liver cells in a monolayer on the surface of the glass slide; and the specimen cell objects 15 are human cells taken from a breast tumor to be analyzed as to their DNA content. The liquid stain is introduced to cavity 28 to stain the cell objects 15 and/or 17 for either quantitative or qualitative analysis. In order to provide as uniform a staining practice as practicable, the staining solution is continuously agitated to continuously mix solvent and solute, and to avoid a concentration gradient in a quiescent bath. In addition, nonreactive sheath 64 on stirring rod 54 prevents pole piece 62 from reacting with the solution to contaminate the solution and disrupt the solute concentration. Although the above-illustration of stirrer subassembly 10 is directed to its use in a Coplin jar it is apparent that the particular shape of housing 50 can be altered to accommodate any small environment and generally any reasonable shape.

While only a specific embodiment of the invention has been described and shown, it is apparent that various alterations and modifications can be made therein. It is therefore, the intention in the appended claims to cover all such modifications and alterations as may fall within the scope and spirit of the invention.

What is claimed is:

1. An apparatus for staining simultaneously specimen and calibration cell objects on each of a plurality of slides comprising;
   a container for containing a liquid stain having a wall through which magnetic flux may pass,
   spacers in the container for separating adjacent slides and for holding the slides aligned in a row,
   a cage positioned in the container having a hollow interior and a plurality of perforations through which the liquid stain may flow into and from the cage,
   a magnetic stirrer in the cage for stirring and agitating the liquid stain to pass into and from the cage and for causing the liquid stain in the container to become more uniform and to flow across the specimen and calibration cell objects in a row of slides in the container to stain the specimen cells and the calibration cells spaced vertically on each slide with substantially the same uniform stain, and
   a magnetic drive unit positioned outside of the container wall and using magnetic flux travelling through the container wall to rotate the magnetic stirrer to stir and mix uniformly the liquid stain as it stains specimen and calibration cell objects on the slides in the container.

2. An apparatus in accordance with claim 1 in which the slides have calibration cell objects on one end and specimen cell objects on the other end of the slides and in which the stain is Thionin.

3. An apparatus in accordance with claim 1 in which the magnetic stirrer is a small rod, said cage being in the shape of a box having walls with a plurality of perforations therein.

4. An apparatus in accordance with claim 1 in which the magnetic drive unit has a flat upper surface, said container may be placed upon and lifted from the upper surface, and in which a lower end of slide rests on the top of the cage.

5. A magnetic stirrer subassembly operable with a magnetic stirrer drive for stirring a solution in a reaction vessel for specimens and samples, said subasssembly comprising:
   a housing defining an enclosure with a plurality of perforations communicating through said housing to said enclosure;
   a magnetically responsive stirring rod retained and rotatable in said housing enclosure to isolate said stirring rod from said samples;
   said stirring rod rotatable by said magnetic stirrer drive to agitate said solution in said vessel.

6. A method of staining calibration slides having calibration cell objects and specimen cell objects spaced from each other on the slide, said method comprising the steps of:
   providing slides having calibration cell objects and specimen cell objects spaced from each other on the slide,
   providing a staining container having spaced ribs therein and positioning the slides between adjacent ribs with the specimen cells all at the same vertical height in the container,
   positioning each of several slides in a row and in spaced relationship in the staining container for receiving a liquid stain having a predetermined stain concentration,
   providing a magnetic stirring element in the staining container to agitate the stain to prevent separation of the stain at different levels in the container, and
   locating the container and magnetic stirring element in close proximity to a magnetic drive exterior of the container and stain and driving the stirring element by magnetic force to agitate and circulate the stain in the container to provide a uniform stain for both the specimen cell objects and the calibration cell objects,
   placing the lower ends of the slides on an upper side of a perforated cage; and
   staining both the specimen cell objects and the calibration cell objects with a uniform staining liquid by flowing stain through perforations in the cage to cause an agitation of the liquid stain being stirred by the stirring element within the cage.

* * * * *